(12) United States Patent
Nackaerts et al.

(10) Patent No.: US 8,957,687 B2
(45) Date of Patent: Feb. 17, 2015

(54) SENSOR

(75) Inventors: Axel Nackaerts, Heverlee (BE); Matthias Merz, Leuven (BE); Youri Victorovitch Ponomarev, Leuven (BE)

(73) Assignee: NXP, B.V., Eindhoven (NL)

( * ) Notice: Subject to any disclaimer, the term of this patent is extended or adjusted under 35 U.S.C. 154(b) by 274 days.

(21) Appl. No.: 13/457,072

(22) Filed: Apr. 26, 2012

(65) Prior Publication Data

US 2012/0286803 A1 Nov. 15, 2012

(30) Foreign Application Priority Data

May 9, 2011 (EP) .................................... 11165350

(51) Int. Cl.
*G01R 27/28* (2006.01)
*G01N 27/414* (2006.01)
(52) U.S. Cl.
CPC .................................... *G01N 27/414* (2013.01)
USPC ............................ 324/649; 324/438; 324/464
(58) Field of Classification Search
USPC ................ 324/452, 453, 71.1, 649, 71.5, 438
See application file for complete search history.

(56) References Cited

U.S. PATENT DOCUMENTS

| | | | |
|---|---|---|---|
| 4,397,714 A | 8/1983 | Janata et al. | |
| 7,632,670 B2 | 12/2009 | Offenhausser et al. | |
| 2004/0056016 A1* | 3/2004 | Tian et al. | 219/408 |
| 2005/0230271 A1 | 10/2005 | Levon et al. | |
| 2007/0148847 A1* | 6/2007 | Han | 438/199 |
| 2009/0014757 A1 | 1/2009 | Takulapalli et al. | |
| 2010/0066378 A1* | 3/2010 | Ahmadi et al. | 324/429 |
| 2010/0270174 A1 | 10/2010 | Chen et al. | |
| 2011/0036913 A1 | 2/2011 | Merz et al. | |
| 2011/0156177 A1 | 6/2011 | Merz | |
| 2011/0175595 A1 | 7/2011 | Nackaerts et al. | |

FOREIGN PATENT DOCUMENTS

| | | |
|---|---|---|
| DE | 101 63 557 A1 | 10/2003 |
| GB | 2 103 014 A | 2/1983 |
| WO | 2005/121765 A1 | 12/2005 |

OTHER PUBLICATIONS

Extended European Search Report for European patent appln. No. 11165350.7 (Oct. 13, 2011).
Office Action from counterpart application No. CN201210138964.3 (Dec. 12, 2013).
Office Action from counterpart application No. CN 201210138964.3 (May 20, 2014).

* cited by examiner

*Primary Examiner* — Vincent Q Nguyen

(57) ABSTRACT

The invention relates to an electrochemical sensor integrated on a substrate, the electrochemical sensor including: a field effect transistor integrated on the substrate and having a source, gate and drain connections, said gate of the field effect transistor including: a sensing gate conductively coupled to a sensing electrode; and a bias gate, wherein the sensing gate is capacitively coupled to the bias gate and the bias gate is capacitively coupled to the substrate.

13 Claims, 2 Drawing Sheets

EGFET + cap + reset transistors

SENSOR

CROSS-REFERENCE TO RELATED APPLICATIONS

This application claims the priority under 35 U.S.C. §119 of European patent application no 11165350.7, filed on May 9, 2011, the contents of which are incorporated by reference herein.

FIELD OF THE INVENTION

The present invention relates to electrochemical sensors and in particular to electrochemical sensors comprising field effect transistors. More particularly the present invention relates to fluid pH sensors or ion sensors.

The present invention also relates to an integrated circuit comprising such an electrochemical sensor.

The present invention also relates to method of performing a measurement using such a sensor, or to a method of measurement using an integrated circuit comprising said sensor.

BACKGROUND OF THE INVENTION

Field effect transistors (FETs) may be used as sensors by utilising the gate electrode of the FET as a sensor electrode. The gate electrode may be coated with or formed from a substance that can interact with a fluid analyte such that the operation of the FET becomes sensitive to, for example, chemical compounds, particles or ions contained in the analyte. Such sensors have applications as pH sensors. In applications the electrical current through FET based sensors may be dependent on the concentration of the chemical compound in the analyte when the analyte is in contact with the gate electrode of the FET.

One particular advantage of using FET based sensors is that they may be easily integrated into an integrated circuit package, such that the signal processing components associated with, and/or ancillary to the sensor can be provided on the same semiconductor die, thus yielding a compact sensor arrangement and lower manufacturing costs. Furthermore, by integrating sensors into an integrated circuit package processing of the entire sensor integrated package can be simplified.

However, for FET based sensors it may be necessary to separate the gate electrode from the analyte such that the gate electrode is not in contact with the analyte. Separating the gate electrode from the analyte prevents any contact between the analyte and the gate electrode which could result in chemical reactions between the analyte and gate electrode irreparably damaging the FET.

One particular arrangement of a FET based sensor which separates the gate electrode and analyte utilises an extended gate electrode FET (EGFET) arrangement. The EGFET structure may comprise a gate electrode, which is electrically connected to a measurement electrode, and a reference electrode. The measurement electrode and reference electrode may be in contact with the analyte. The EGFET will begin to exhibit a current flow through the FET when the potential difference between the gate electrode and the reference electrode, caused by the analyte, exceeds a threshold voltage of the EGFET. The threshold voltage is the voltage at or near which the EGFET begins to conduct.

However, one problem with the known EGFET arrangements is that the potential difference between the measurement electrode and the reference electrode, caused by the analyte, may not be greater than the threshold voltage of the FET due to, for example, low concentrations of chemical compounds in the analyte. By applying a bias voltage to the gate electrode and the reference electrode it may be possible to lower the threshold voltage of the FET. However, the bias voltage may cause an unwanted electrical current to flow through the analyte causing chemical reactions in the fluid analyte which may result in sensor drift and/or corrosion of the measurement electrode and/or the reference electrode which can adversely affect the predictability and accuracy of the sensor.

SUMMARY OF INVENTION

The present invention seeks to provide an electrochemical sensor which overcomes the above mentioned problems. The present invention also seeks to provide a method of measurement and an integrated circuit comprising said sensor which overcomes said problems.

Thus, according to a first aspect of the present invention there is provided An electrochemical sensor integrated on a substrate, the electrochemical sensor comprising: a field effect transistor integrated on the substrate and having source, gate and drain connections, said gate of the field effect transistor comprising: a sensing gate conductively coupled to a sensing electrode; and a bias gate, wherein the sensing gate is capacitively coupled to the bias gate and the bias gate is capacitively coupled to the substrate.

Preferably a first oxide layer capacitively couples the bias gate to the sensing gate. Preferably a second oxide layer capacitively couples the bias gate to the substrate. Preferably the first oxide layer is an oxide-nitride-oxide material and the second oxide layer is a tunnel oxide material. By capacitive coupling the invention provides galvanic isolation of the sensing electrode from the bias gate. The sensor of the present invention therefore provides independent biasing of the sensing gate and the bias gate due to the capacitive coupling of the sensing gate and the bias gate. It also provides for dynamically tuning of the electrochemical sensor for a particular sensitivity or input voltage range. The present invention can therefore mitigate charge leakage from a liquid analyte to the sensor. Moreover it seeks to reduce the associated drift in the drain current of the FET due to the changing gate voltage brought about by the analyte.

Preferably the sensing gate is connected to a first bias voltage via a first control switch and the bias gate is connected to a second bias voltage via a second control switch. The sensor of the present invention therefore provides for independent biasing of the gate of an EGFET and the analyte while using the same device die area as known conventional EGFETs. The control switches may be reset transistors. The reset transistors may be formed on the same substrate as the FET. A combination of single-gate and dual-gate stacks may be used to form the reset transistors. This allows for reduced sensor device footprint and therefore improved integration with additional electronic control devices and/or sensors such as humidity, temperature or pressure sensors. The sensor according to the invention can be manufactured in an integrated circuit package.

According to a second aspect the present invention provides an integrated electronic circuit comprising the sensor of the first aspect.

According to a third aspect of the invention there is provided a method of performing a measurement with the sensor of the first aspect, comprising: measuring a potential at said sensing electrode; biasing a liquid analyte to a potential based on the potential at said sensing electrode; biasing the sensing gate, biasing the source and drain to enable current to flow through the field effect transistor; biasing the bias gate; and reading the current flowing through the field effect transistor.

Preferably, the liquid analyte is biased to maintain a net zero potential difference between the sense electrode and the liquid analyte. The present invention can therefore mitigate charge leakage from a liquid analyte to the sensor which may result in erroneous measurements.

DESCRIPTION OF THE DRAWINGS

The invention is described further hereinafter by way of example only with reference to the accompanying drawings in which.

Figure 1:
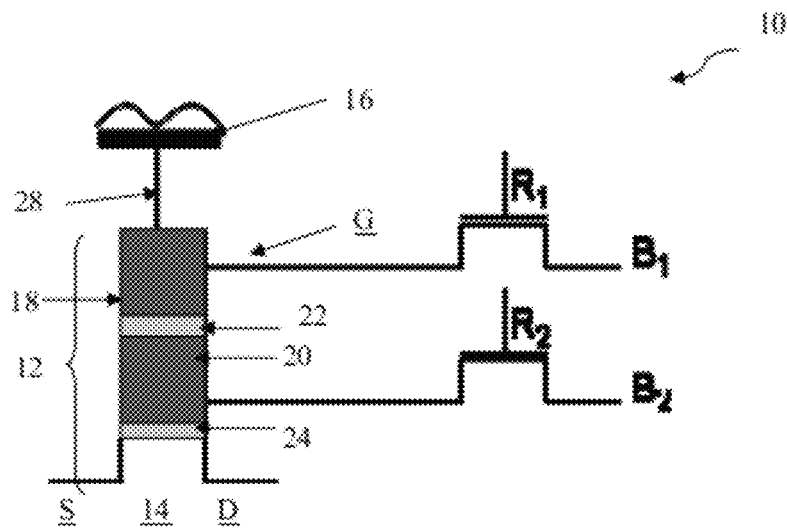
FIG. 1 is a schematic view of the electrochemical sensor and associated control circuit.

In overview, as shown in FIG. 1, the sensor 10 comprises a field effect transistor (FET) 12 formed on a substrate 14, and sensing electrode 16 conductively coupled to the FET 12. Reset transistors R1 and R2 are conductively connected to the FET 12 to switchably apply respective bias voltages B1 and B2 to the FET 12. The FET 12 and sensing electrode 16 provide a sensing functionality of the sensor 10, whereas the reset transistors R1 and R2 provide a control functionality of the sensor 10. The FET also includes respective source (S) and drain (D) gates.

Referring to FIG. 1, the structure of the FET 12 can be described as follows. The gate G of the FET 12 is formed of a sensing gate 18 and a bias gate 20. The sensing gate 18 is stacked on top of the bias gate 20. A first insulating oxide layer 22 is provided between the sensing gate 18 and the bias gate 20, and second insulating oxide layer 24 is provided between the substrate 14 and the bias gate 20. As a result of the first insulating oxide layer 22 the bias gate 20 is electrically isolated from the sensing gate 18. As a result of the second oxide layer 24, the bias gate 20 is electrically isolated from the substrate 14. In this way the sensing gate 18 can be said to be galvanically decoupled (or isolated) from the bias gate 20 and the bias gate 20 is galvanically decoupled from the substrate 14. The first insulating oxide layer 22 may be an oxide-nitride-oxide (ONO) material layer. The second insulating oxide layer 24 may be a tunnel oxide material layer. In general therefore the gate G of the FET 12 is formed as a dual-gate stack of conducting layer-dielectric layer-conducting layer-dielectric layer formed on a substrate 14. The sensing electrode 16 and sensing gate 18 may be an extended gate electrode (EGFET) arrangement. The FET 12 and electrodes may be fabricated by any appropriate means as would be understood by the skilled person.

The above structure is therefore arranged so that the sensing gate 18 is conductively coupled to the sensing electrode 16 via a conductive connection 28, such that the sensing electrode 16 and the sensing gate 18 are at the same potential (voltage). The sensor 10 is arranged such that the sensing electrode 16 can be in contact with the analyte and therefore any voltage induced by the analyte at the sensing electrode 16 will be equal to the potential at the sensing gate 18 due to an electrically conductive connection 28 therebetween.

By way of a non-limiting example, the skilled person will recognise that the voltage generated by the analyte at the sensing electrode 16 may result from chemical binding of the analyte with the sensing electrode 16. As a result of the generated voltage a current will flow through the FET 12 when the voltage exceeds a threshold voltage Vth of the FET 12.

Due to the use of the first and second insulating oxide layers 22, 24 and the extended gate electrode arrangement, the FET 12 may be termed a dual-poly extended gate FET (DPEGFET), where the term poly refers to the use of polysilicon as a generic example of the respective first 22 and second 24 oxide layers. As the skilled person will recognise the poly-silicon oxide layers may be replaced with by any appropriate dielectric materials provided that the sensing gate 18 is galvanically decoupled from the bias gate 20 and the bias gate 20 is galvanically decoupled from the substrate 14.

Figure 2:
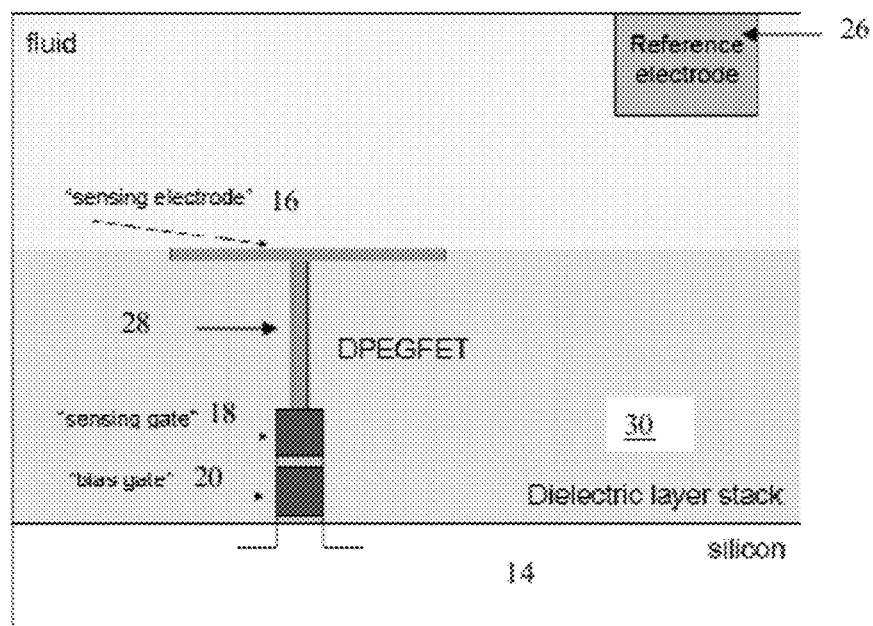
FIG. 2 is schematic cross-sectional view of the layout of the electrochemical sensor.

Referring now to FIG. 2, the sensing electrode 16 is arranged such that it can directly contact the analyte of interest. Similarly, a reference electrode 26 is arranged such that it may directly contact the analyte. The sensing electrode 16 and reference electrode 26 may be arranged such that they form part of a fluidic chamber or conduit suitable for holding and/or channelling the analyte.

The sensing electrode 16 is connected to the sensing gate 18 via the electrically conductive connection 28. A dielectric layer stack 30 may be provided to encapsulate and protect the FET 12 and conductive connection 28 from harmful exposure to the analyte and/or the atmosphere. Each of the reset transistors R1, R2 may be formed on the same substrate 14 as the FET 12. The sensing electrode 16 and the bias electrode 18 are conductively coupled to the respective reset transistors R1 and R2. By way of a non-limiting example the reset transistors R1 and R2 may be single gate transistors which act to controllably bias the sensing gate 18 and the bias gate 20 respectively. Alternatively, the reset transistors R1, R2 may be dual gate transistors.

Figure 3:
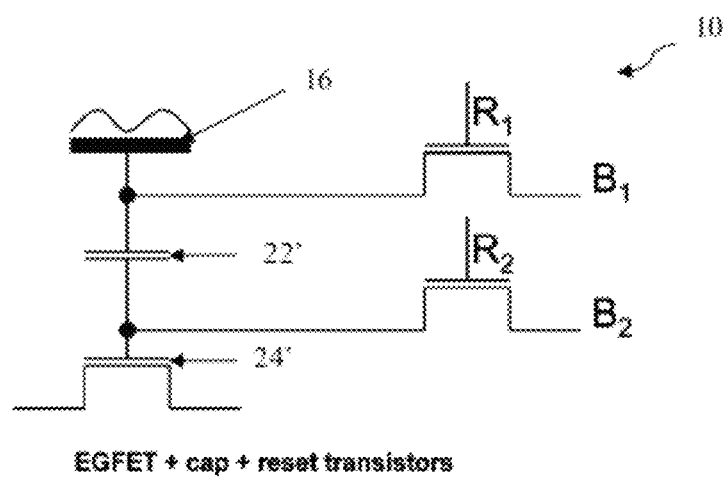
FIG. 3 is an equivalent circuit diagram of the electrochemical sensor and associated control circuit of FIG. 1.

Referring to FIG. 3 the operation of the sensor will now be described. The oxide layers 22 and 24 effectively act as the dielectric of a capacitor thus preventing charge from crossing the either of the first and second oxide layers 22 and 24. The first and second oxide layers 22 and 24 act as the dielectric of a plate capacitor. Therefore, FIG. 3 represents an equivalent circuit of the structure depicted in FIG. 1, where the first and second oxide layers 22 and 24 are represented by respective capacitances 22' and 24'.

In the following description it will be assumed that the reset transistors R1 and R2 have an effective zero resistance when closed and an effective infinite resistance when open. In the latter case this means that there is no leakage current through the reset transistors R1, R2 during operation of the sensor 10.

In operation, the sensor 10 operates in two stages, namely (1) the measurement stage and (2) the read-out stage.

During the measurement stage, as the name implies, the potential difference generated by the analyte at the sense electrode 16 is measured. In the measurement stage each of the reset transistors R1 and R2 are opened such they have infinite resistance and therefore no bias voltage B1 or B2 is applied to the sensing gate 18 and the bias gate 20. The liquid analyte is then biased to a potential $V_{fluid}$ by the reference electrode 26. For the sake of brevity the reference electrode 26 biasing is not shown, however it may utilise a similar biasing arrangement as the sensing gate 18 or the bias gate 20. Furthermore, the reset transistors R1 and R2 can be controlled by any appropriate control circuitry (not illustrated).

Typically the voltage of $V_{fluid}$ is 0V. However, $V_{fluid}$ may be varied or dynamically tuned to a positive or negative voltage in cases where it is difficult to obtain a reading from the analyte. Situations where it is difficult to obtain readings may for example be as a result of small concentrations of particles and/or ions in the analyte. Therefore, it is possible adjust the potential of the sensing gate 18 or the fluid analyte such that the voltage difference between the sensing gate 18 and the fluid are within acceptable limits.

In operation, if due to a chemical reaction in the fluid, the potential of the liquid shifts to a higher or lower voltage V2, a potential difference of V2-V1 now exists at the sensing electrode 16. It is therefore possible to adjust either the bias of the sensing gate 18 to V2, or the bias of the liquid to V1 to maintain a net 0V potential difference, thereby mitigating any potential problems as discussed above. In particular as discussed it is advantageous to avoid electro-chemical reaction between surface and fluid. 0V may be a typical net potential difference, but positive or negative voltages may be used, depending on the chemical composition of the fluid.

The sensing gate 18 is then biased to voltage B1 by closing reset device R1. B1 is equal to $V_{fluid}$ which prevents unwanted electrical current flowing through the analyte which may causing unwanted chemical reactions between the sensing electrode 16 and the analyte. As a non-limiting example $V_{fluid}$=B1=0 Volts. The source S and drain D of the FET 12 are then biased to enable conduction through the FET 12. The reset device R1 is then opened and the bias gate 20 is then biased to a potential B2 such that the FET is in a conduction state. The current flowing through the FET 12 is called the reference current and typically when B2>Vth, where Vth is the threshold voltage of the FET 12, the FET 12 begins to conduct.

During the read-out stage both the reset devices R1 and R2 are closed and read-out of the measured current flowing through the FET 12 due to the potential induced at the sense electrode 16 begins.

The FET 12 may have a threshold voltage Vth of 0.4 V. Therefore during operation of the sensor 10 the following voltage biasing may be used. The fluid is biased at 0 V for the reference condition (that is where the pH is known). The sensing gate 18 is biased at 0 V to avoid unwanted electrical current flowing through the analyte which may cause unwanted chemical reactions between the sensing electrode and the analyte. The bias gate 20 is biased at 0.7 V (that is Gate-Source Voltage is greater than the threshold voltage, Vgs>Vth) to create an inversion channel in the FET. The source-drain voltage Vds is set to 0.2 V so that the FET operates in linear (triode) mode, that is Vds<(Vgs-Vth).

Typically a change in 1 pH of the analyte results in a 59.2 mV shift of fluid potential at a temperature of 298 K according to the Nernst equation (Wahl (2005). "A Short History of Electrochemistry". *Galvanotechnik* 96 (8): 1820-1828). This shift in potential is capacitively coupled to the channel of the FET by a ratio of the Cfluid-sense, Csense-bias and Cbias-substrate gate capacitances. This results in a change in current flowing through the FET proportional to the potential shift due to the pH change.

Csense-bias is the capacitance between the bias gate and the sensing gate; and Cbias is the capacitance of the bias gate to the FET 12 conduction channel, commonly known as Cox in FET technology. Csense/Cbias determines the coupling strength of the oxide capacitances. Where the oxide layers can be described as a series connection of capacitors.

The above voltage levels are provided here merely as an example. The skilled person would recognise that alternative voltages may be chosen depending on circuit boundary conditions such as, for example noise, power consumption and so forth.

In operation the FET 12 acts as a variable current source. The current flowing through the FET 12 would typically be copied to circuitry (not illustrated), such as an analog-to-digital converter using a current mirror (not illustrated) thereby keeping the output current constant regardless of loading. The copied current is then used either directly by the current-driven analog-to-digital converter, or first directed to a current-to-voltage converter and sampled by a voltage-input analog-to-digital converter. There are many existing methods to measure the current flowing through the FET 12.

In view of the foregoing description it will be evident to a person skilled in the art that various modifications may be made within the scope of the invention. If the properties of the liquid analyte change (e.g. the pH), the potential of the sense electrode 16 will change, and that change is seen at the sensing gate 18, and through capacitive coupling, also at the bias gate. This will induce a change in current flowing through the FET 12. The relative change in current, as scaled by the current voltage (IN) characteristics of the FET is proportional to the change in potential at the sensing electrode 16. The sensitivity of the sensor 10 can therefore be set at design-time by optimizing the area of the sensing gate 18, bias gate 20, and sensing electrode 16, where the skilled person can determine the optimum coupling capacitance between these three nodes of the sensor 10.

The substrate 14 may be formed of any suitable material, for example Silicon or Silicon Oxide. As an alternative to the reset transistors R1 and R2, the skilled person would recognise that any device with switching capability may be utilised. For example the transistor may be replaced by pass-gates, combinations of NFET and PFET devices, galvanic switches and so on.

As a result, the senor 10 according to the present invention provides for a new and improved EGFET based pH sensor.

Particular and preferred aspects of the invention are set out in the accompanying independent claims. Combinations of features from the dependent and/or independent claims may be combined as appropriate and not merely as set out in the claims.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived there from. In particular, with reference to the appended claims, features from dependent claims may be combined with those of the independent claims and features from respective independent claims may be combined in any appropriate manner and not merely in specific combinations enumerated in the claims.

Features which are described in the context of separate embodiments may also be provided in combination in a single embodiment. Conversely, various features which are, for brevity, described in the context of a single embodiment, may also be provided separately or in any suitable sub combination.

For the sake of completeness it is also stated that the term "comprising" does not exclude other elements or steps, the term "a" or "an" does not exclude a plurality, a single processor or other unit may fulfil the functions of several means recited in the claims and reference signs in the claims shall not be construed as limiting the scope of the claims.

The invention claimed is:

1. An electrochemical sensor integrated on a substrate, the electrochemical sensor comprising:
a field effect transistor integrated on the substrate and having source, gate and drain connections,
a gate of the field effect transistor comprising:

a sensing gate conductively coupled to a sensing electrode; and a bias gate,
wherein the sensing gate is capacitively coupled to the bias gate and the bias gate is capacitively coupled to the substrate; and
wherein the sensing gate is connected to a first bias voltage and the bias gate is connected to a second bias voltage.

2. The sensor of claim 1, wherein a first oxide layer of said gate capacitively couples the bias gate to the sensing gate.

3. The sensor of claim 1, wherein a second oxide layer of said gate capacitively couples the bias gate to the substrate.

4. The sensor of claim 3,
wherein a first oxide layer of said gate capacitively couples the bias gate to the sensing gate; and
wherein the first oxide layer is an oxide-nitride-oxide material layer and the second oxide layer is a tunnel oxide material.

5. The sensor of claim 1 wherein the gate of said field effect transistor is a formed as a dual gate stack.

6. The sensor of claim 5, wherein the sensing gate and the bias gate are independently biased by said respective first and second bias voltages.

7. The sensor of claim 1, wherein the sensing gate is connected to the first bias voltage via a first control switch and the bias gate is connected to the second bias voltage via a second control switch.

8. The sensor of claim 7, wherein at least one of the first control switch and the second control switch are integrated on said substrate.

9. The sensor of claim 1, wherein the field effect transistor is an extended gate field effect transistor.

10. The sensor of claim 1, wherein the field effect transistor is a dual-poly transistor.

11. An integrated electronic circuit comprising the sensor as claimed in claim 1.

12. A method of performing a measurement with the sensor of claim 1, comprising:
measuring a potential at said sensing electrode;
biasing a liquid analyte to a potential based on the potential at said sensing electrode;
biasing the sensing gate,
biasing the source and the drain to enable current to flow through the field effect transistor;
biasing the bias gate; and
reading the current flowing through the field effect transistor.

13. The method of claim 12, whereby the liquid analyte is biased to maintain a net zero potential difference between the sense electrode and the liquid analyte.

* * * * *